United States Patent
Baumgartner et al.

(10) Patent No.: US 11,273,230 B1
(45) Date of Patent: Mar. 15, 2022

(54) MULTI-FUNCTION PRODUCT DISINFECTION CABINET

(71) Applicants: Carl L. Ricciardi, Tomahawk, WI (US); Jonathan J. Ricciardi, Richland, WA (US)

(72) Inventors: Paul Baumgartner, Port St. Lucie, FL (US); Carl L. Ricciardi, Tomahawk, WI (US); Jonathan J. Ricciardi, Wausau, WI (US)

( * ) Notice: Subject to any disclaimer, the term of this patent is extended or adjusted under 35 U.S.C. 154(b) by 586 days.

(21) Appl. No.: 15/947,896

(22) Filed: Apr. 9, 2018

Related U.S. Application Data

(60) Provisional application No. 62/483,486, filed on Apr. 10, 2017.

(51) Int. Cl.
| | |
|---|---|
| *A61L 2/26* | (2006.01) |
| *A61L 2/24* | (2006.01) |
| *A61L 2/22* | (2006.01) |

(52) U.S. Cl.
CPC .............. *A61L 2/26* (2013.01); *A61L 2/22* (2013.01); *A61L 2/24* (2013.01); *A61L 2202/14* (2013.01); *A61L 2202/24* (2013.01)

(58) Field of Classification Search
CPC ..... A61L 2/26; A61L 2/22; A61L 2/24; A61L 2202/14; A61L 2202/24
See application file for complete search history.

(56) References Cited

U.S. PATENT DOCUMENTS

| | | | | |
|---|---|---|---|---|
| 3,777,508 | A * | 12/1973 | Imabayashi | F24F 3/153 62/324.3 |
| 8,506,900 | B1 * | 8/2013 | Ricciardi | A61L 2/04 422/292 |
| 2002/0044898 | A1 * | 4/2002 | Sergio | A61L 2/18 422/300 |
| 2003/0208115 | A1 * | 11/2003 | Kime | A61B 8/12 600/407 |
| 2015/0374868 | A1 * | 12/2015 | Bruce | A61L 2/208 422/3 |
| 2018/0325367 | A1 * | 11/2018 | Iwasaki | A61B 90/70 |

* cited by examiner

*Primary Examiner* — Sean E Conley
*Assistant Examiner* — Brendan A Hensel
(74) *Attorney, Agent, or Firm* — Donald J. Ersler

(57) ABSTRACT

A multi-function product disinfection cabinet preferably includes a sealed test cabinet, a high level disinfection system, a dehumidifier, an electrical function tester and a bar code reader. The sealed test cabinet preferably includes a sealed test chamber, a rear dehumidifier chamber and a rear droplet chamber. The high level disinfection system includes an aerosol blower, an aerosol generator, aerosol tubing and an aerosol control module. The aerosol blower blows a treatment substance from the aerosol generator into the sealed test chamber. The dehumidifier preferably includes components of an air conditioner. Air blowing upward from a chamber air blower dries products disinfected and tested in the sealed test chamber. An electrical function tester preferably includes an electronic test module, a plurality of test sockets and a plurality of interface test blocks. The bar code reader is used to read identification information from a cable or component.

20 Claims, 4 Drawing Sheets

MULTI-FUNCTION PRODUCT DISINFECTION CABINET

1. CROSS-REFERENCES TO RELATED APPLICATIONS

This is a utility patent application, which claims the benefit of provisional application No. 62/483,486 filed on Apr. 10, 2017.

BACKGROUND OF THE INVENTION

2. Field of the Invention

The present invention relates generally to the cleaning, sanitization, disinfection, high level disinfection of pathogenic contaminated patient monitoring equipment and more specifically to a multi-function surface treatment and/or surface cleaning chamber and/or enclosure, and even more specifically to a multi-function product sanitization, disinfection, and/or sterilization cabinet, which allows for preferably, but not limited to, low temperature decontamination, sanitization, disinfection or sterilization of products such as, but not limited to medical equipment and/or their various components and electrical testing of these same products and/or various components while achieving, without limitation, a greater than 6 log reduction of bio burden in less than 10 minutes. More generally, the present invention relates to an apparatus that can not only treat the surfaces of various object(s), components, and equipment, in a manner to achieve a result on their surfaces such as, but not limited to, sanitization, disinfection, and/or sterilization, but also effectively test the one or more object(s), such as, component(s), instrument(s) and/or equipment(s), for their effective function and performance, and more particularly any optical, physical, mechanical, and/or electrical function(s) and performance(s), at any time before, during, and/or after, any part of any surface treatment or decontamination cycle.

3. Discussion of the Prior Art

It appears that the prior art does not teach or suggest a multi-function product disinfection cabinet, which allows for low temperature disinfection of medical equipment that can achieve a greater than 6 log reduction in less than 10 minutes. More Specifically, the prior art does not teach or suggest a multi-function surface treatment enclosure that can clean, sanitize, disinfect, or sterilize the surfaces of any object and then test and check its function and/or performance before, during, and/or after their various surfaces are treated or decontaminated. In the clinical health care setting, certain instruments, diagnostic tools, and monitoring accessories, are essential for routine patient care. Generally, they are high-use, high-touch medical products and are constructed of materials that are not safe for high temperature disinfection methods including autoclaving. Because of their material makeup and dimensions they are not regularly cleaned sufficiently to eliminate cross-contamination from one patient to the next. The current method of cleaning by hand using strong chemicals tends to degrade the protective coating of the medical products.

In addition, patient monitoring leads, probes, sensors and instruments routinely fail through repeated use, hand cleaning, abuse, mishandling, and stress. If this condition is not timely diagnosed, these instruments can be transferred from room to room, patient to patient, until eventually diagnosed and identified as defective. Inventory, storage, and availability are major considerations in busy clinical treatment areas.

Recent published scientific literature has shown that antibiotic resistant pathogenic bio-burden including, but not limited to Super Bugs, is found primarily in the hospital and clinic setting. Further, there is an unanimity of thought within the medical community, that the transmission of infectious disease is spread from patient to patient by many vectors including improperly disinfected equipment. Because many of the serious diseases are spread by the hands of health care workers and by the patient touching the surfaces in his/her immediate vicinity as well as bowel and bladder function, perspiration, coughing or sneezing, it is paramount that all surfaces of patient related equipment are disinfected including the patient monitoring products that have been in direct patient contact.

Trial and error is a common approach to selecting suitable/reliable cable and/or wire leads, probes and devices. Currently, lacking a comprehensive methodology for disinfection, storage and grouping of like devices, hospitals have adopted a variety of less than optimal, methods for inventory control, testing, and securing replacement of items. This function usually defaults to the clinical end user at the most inopportune or inconvenient time.

Most hospitals have trained biomedical technicians that can be dispatched on an as needed basis to assist in troubleshooting patient monitoring equipment issues, but unavailability and prior commitment usually forces users to borrow the needed components from available sources creating inventory confusion and uncertainty as to the cleanliness, function, performance, and safety of the equipment.

This practice often results in questionable or defective items remaining in clinical areas available for others to use without knowing the component(s) functional condition or if it had been evaluated for electrical safety and whether it had been effectively disinfected. Often times clinical accessory items cannot be determined to be acceptable or unacceptable based on visual inspections alone. When defective items are inter-mixed with good items, the patient is put at risk for electrical injury and/or contamination. Troubleshooting various medical components, in clinical areas with limited availability of appropriate test equipment, resources, or skills, can impact diagnosis and timeliness of patient treatment. Sophisticated electronic test equipment necessary to diagnose electronic failure is not available in the area where these devices are routinely used.

Having convenient and timely access to fully tested and disinfected medical equipment probes, and accessories, will greatly improve the quality and safety to both patients and clinical operators. The diagnosis and removal of defective and contaminated equipment will reduce the risk of an electrical injury and pathogenic contamination. Having the items disinfected adds a level of protection against possible cross contamination from previous use on infected patients.

Manual cleaning and checking of the wire and cable leads and probes is often times inconsistent, inadequate and/or incomplete. A system whereby having high-usage reusable components tagged, tracked, function tested, disinfected, and inventoried will greatly improve work flow and operations in the clinical setting.

Accordingly, there is a clearly felt need in the art for a multi-function product disinfection cabinet, which allows for low temperature disinfection of medical equipment, combined with electrical evaluation.

SUMMARY OF THE INVENTION

The present invention provides a multi-function surface treatment enclosure that can both clean, sanitize, disinfect, or sterilize, surfaces of any object intended for use in the health care industry, and then test, qualify, benchmark, and/or check, its function, status, and/or performance. Any effective means, process, and/or technology known to those skilled in the art can be used to clean, sanitize, disinfect, and/or sterilize, (Herein called "Decontaminate") the one or more of any targeted surfaces and/or treated object surfaces, within the one or more of any treatment enclosure(s), cabinet(s), and/or chamber(s), such as, but not limited to any, UV light, vaporized hydrogen peroxide, Peroxyacetic Acid (PAA) gas, any chemical agent in aerosol form, and/or any chemical agent in gas or vapor form. The multi-function product disinfection cabinet allows for low temperature disinfection of medical equipment capable of achieving at least a 6 log reduction of the most difficult to kill bio burden in less than 10 minutes.

The multi-function product disinfection cabinet preferably includes a sealed test cabinet, a high level disinfection system, a dehumidifier, at least one filter, an electrical function tester, a wireless control interface, a bar code reader, compliance reporting software and tracking software. The sealed test cabinet preferably includes a sealed test chamber, a top equipment space, a bottom equipment space, a rear dehumidifier chamber and a rear droplet chamber. The high level disinfection system includes an aerosol blower, an aerosol generator, aerosol tubing and an aerosol control module. U.S. Pat. No. 9,551,996 to Baumgartner et al. describes the elements of the aerosol generator and is herein incorporated by reference in its entirety. An inlet of the aerosol blower communicates with the sealed test chamber and an outlet of the aerosol blower is connected to an inlet of the aerosol generator. The aerosol blower blows air into the inlet of the aerosol generator and may also assist in drawing disinfectant aerosol from the reservoir of disinfectant. An inlet of the aerosol tubing is connected to an outlet of the aerosol generator and an outlet of the aerosol tubing communicates with the sealed test chamber. The aerosol control module controls the operation of the components of the high level disinfectant system. The high level disinfection system is preferably located in the top equipment space.

The dehumidifier preferably includes an evaporator coil 60, a condenser coil and an air conditioning compressor. An outlet of the air conditioning compressor is connected to an inlet of the evaporator coil. The air conditioner compressor pumps refrigerant through the evaporator coil and the condenser coil. The evaporator coil is located inside the dehumidifier chamber. The condenser coil is located in the droplet chamber. The air conditioning compressor is preferably located inside the bottom equipment space. Moisture in the air condenses on the evaporator coil and then drops into a liquid collection bottle. The at least one filter includes filtering of any airborne particles, vapors, or gases. A diverter valve is located in the bottom equipment chamber. The diverter valve includes a humidifier chamber inlet, a droplet inlet and outlet. The diverter valve shuttles between the humidifier chamber inlet and the droplet inlet. The outlet of the diverter valve is connected to an inlet of an air blower. An outlet of the air blower is coupled to a diffuser. The diffuser is located in a bottom of the sealed test chamber. Air blowing upward from the diffuser dries the products disinfected and tested in the sealed test chamber. The air from the diffuser passes through a dehumidifier screen and a droplet screen near at top of the sealed test chamber. The air travels through the humidifier and droplet screens into the rear dehumidifier chamber and the rear droplet chamber.

A disinfectant reservoir and a water reservoir are preferably located in the top equipment space. Disinfectant from the disinfectant reservoir flows into a first inlet of a mixing device and water from the water reservoir flows into a second inlet of the mixing device. An output of the mixing device is connected to the supply reservoir of the aerosol generator. The disinfectant reservoir and the water reservoir may be filed through a fill port located outside the sealed test cabinet. Inlets in a drain manifold draw liquid from numerous places in the sealed test cabinet and an outlet feeds the liquid into a liquid collection bottle. The liquid collection bottle is preferably removed from a front of the sealed test cabinet. The aerosol control module includes the electronic devices and software needed to control the operation of the disinfection system, dehumidifier and communicates with the electrical function tester. The wireless control interface preferably controls the operation of the aerosol control module through a touch screen interface. The wireless control interface includes wireless communication through Bluetooth and WIFI protocols.

An electrical function tester preferably includes an electronic test module, a plurality of test sockets, a plurality of interface test blocks and a bar code reader. The electronic test module includes the compliance software, the tracking software and the software to inventory tested electrical cables or components and reports testing compliance connected to one of the plurality of test sockets. The bar code reader is used to read a bar code, radio frequency identification tag, or other electronically imbedded coding circuit, which is used to identify each electrical cable or component placed in the testing disinfection chamber. The output of the bar code reader is connected to the electronic test module. The plurality of interface test blocks include but are not limited to: an ECG interface test block, a SPO2 interface test block, a IBP interface test block, a TEMP interface test block and a TOCO interface test block. Each interface test block preferably includes a base portion and an extension portion, which extends from the base portion. When needed, the interface test block will include a patient simulation device for providing feedback to a sensor of a particular cable. A plurality of connector pins extends from a back of the base portion. The connector pins are plugged into one of the plurality of test sockets. One end of an electrical cable is plugged into the base portion and an opposing end of the electrical cable is connected to the extension portion. The interface test blocks may also be permanently mounted in the sealed test chamber. The electrical function tester also tests the safety of the electrical cable. The electronic test module is located in the top equipment space.

Accordingly, it is an object of the present invention to provide a multi-function product disinfection cabinet, which provides low temperature disinfection of medical equipment.

Finally, it is another object of the present invention to provide a multi-function product disinfection cabinet, which provides electrical and safety testing of electrical cables and other medical equipment.

These and additional objects, advantages, features and benefits of the present invention will become apparent from the following specification.

DETAILED DESCRIPTION OF THE PREFERRED EMBODIMENTS

Figure 1:
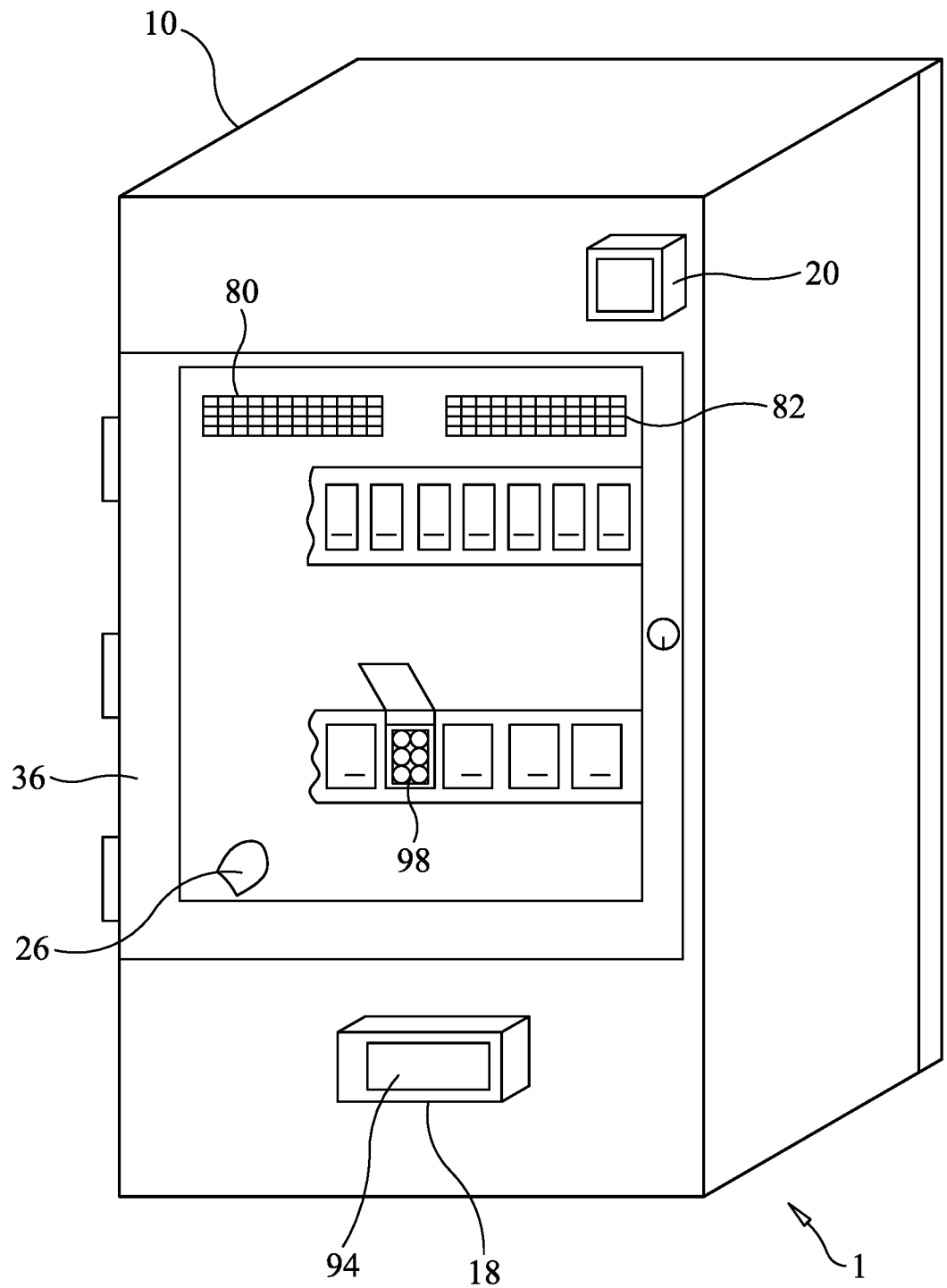
FIG. 1 is a perspective view of a multi-function product disinfection cabinet in accordance with the present invention.
Figure 2:
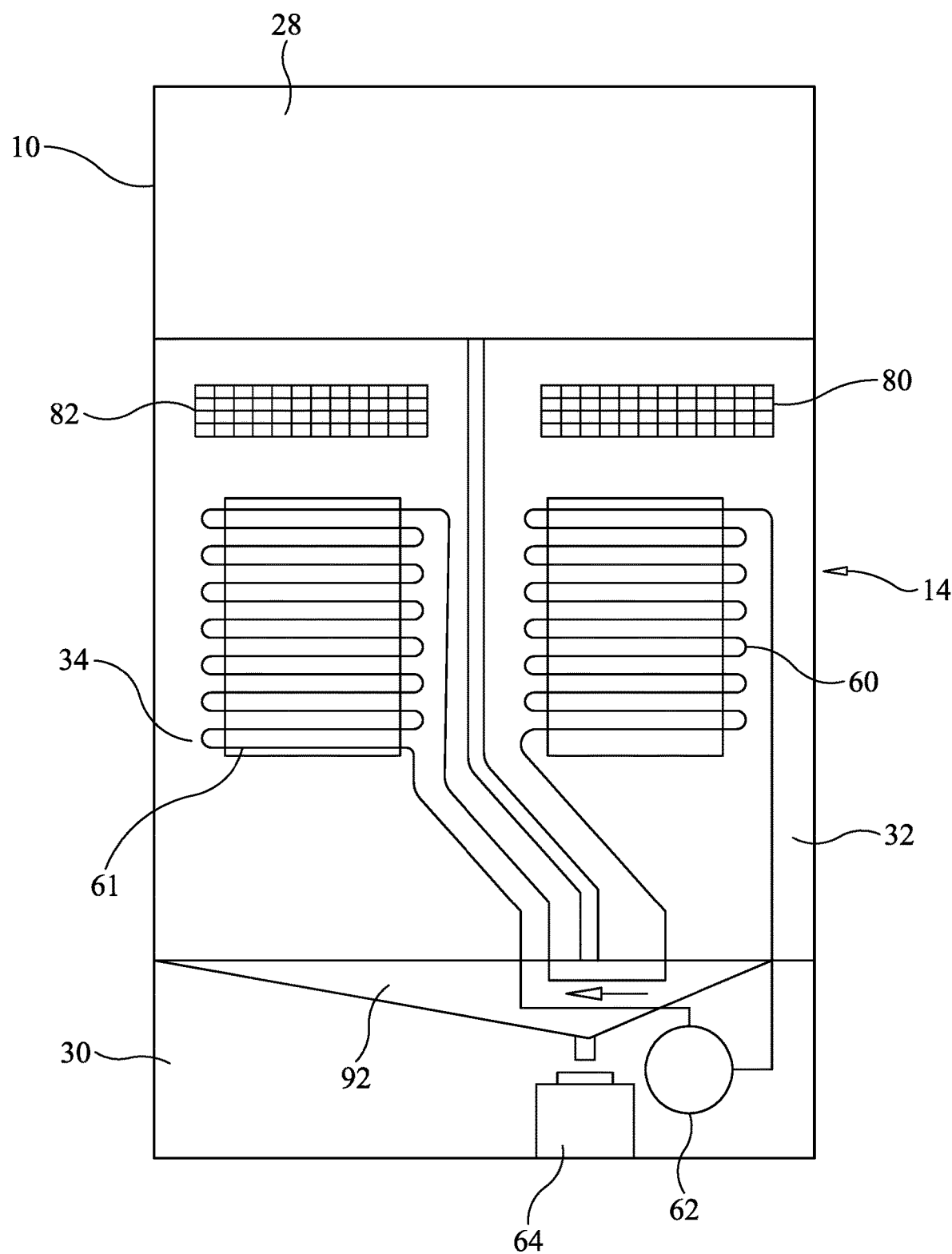
FIG. 2 is a rear view of a multi-function product disinfection cabinet with a rear panel removed to reveal a rear dehumidifier chamber and a rear droplet chamber in accordance with the present invention.
Figure 3:
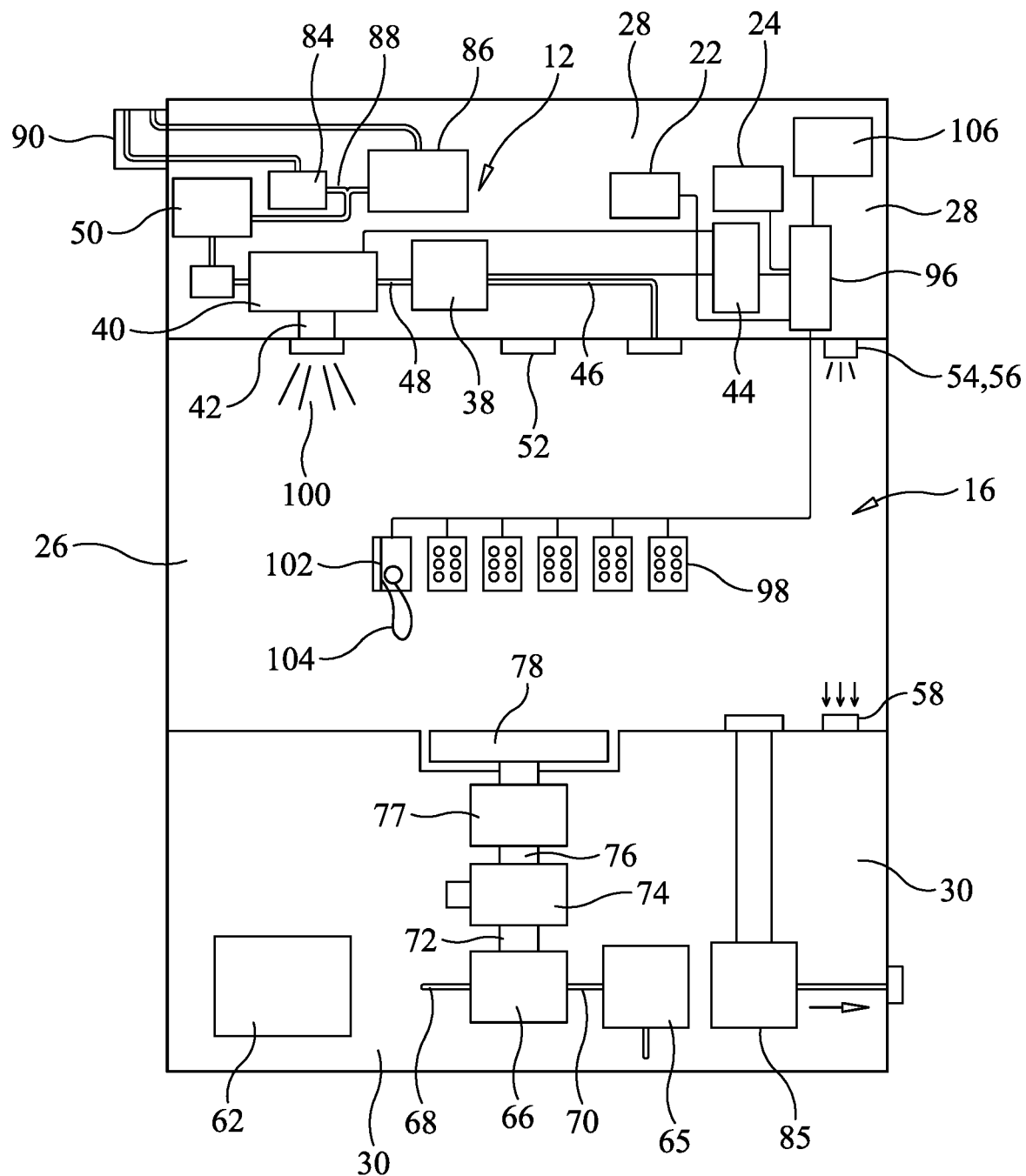
FIG. 3 is a schematic diagram of a portion of a multi-function product disinfection cabinet in accordance with the present invention.

With reference now to the drawings, and particularly to FIG. 1, there is shown a perspective view of a multi-function product disinfection cabinet 1. With reference to FIGS. 2-3, the multi-function product disinfection cabinet 1 preferably includes a sealed test cabinet 10, a high level disinfection system 12, a dehumidifier 14, an electrical function tester 16, a wireless control interface 18, a bar code reader 20, compliance reporting software 22 and tracking software 24. The sealed test cabinet 10 preferably includes a sealed test chamber 26, a top equipment space 28, a bottom equipment space 30, a rear dehumidifier chamber 32, a rear droplet chamber 34 and a sealed door 36.

The high level disinfection system 12 includes an aerosol blower 38, an aerosol generator 40 (device for supplying a treatment substance), aerosol tubing 42 and an aerosol control module 44. U.S. Pat. No. 9,551,996 to Baumgartner et al. describes the elements of the aerosol generator 40 and is herein incorporated by reference in its entirety. An inlet 46 of the aerosol blower 38 communicates with the sealed test chamber 26 and an outlet 48 of the aerosol blower 38 is connected to an outlet of the aerosol generator 40. The aerosol blower 38 blows air into the inlet of the aerosol generator 40 and may also 11 assists in drawing disinfectant aerosol 100 from the reservoir of disinfectant 50. The aerosol 100 includes a droplet size, which is preferably less than 0.7 microns. An inlet of the aerosol tubing 42 is connected to an outlet of the aerosol generator and an outlet of the aerosol tubing 42 communicates with the sealed test chamber 26. The aerosol control module 44 controls the operation of the components of the high level disinfectant system 12. The high level disinfection system 12 is preferably located in the top equipment space 28. It is preferable to have a light 52 to illuminate some types of disinfectant in the sealed test chamber 26. It is also preferable to have a light sensor 54 inside the sealed test chamber 26. The light sensor 54 includes a light source 56 and a light sensor 58. Light is emitted from the light source 56 and received by the light sensor 56 if no disinfectant or an insufficient amount of disinfectant is in the sealed test chamber 26.

The dehumidifier 14 preferably includes an evaporator coil 60, a condenser coil 61 and an air conditioning compressor 62. An outlet of the air conditioning compressor 62 is connected to an inlet of the evaporator coil 60. An outlet of the evaporator coil 60 is connected to an inlet of the condenser coil 61. An outlet of the condenser coil 61 is connected to an inlet of the air conditioner compressor 62. The air conditioner compressor 62 pumps refrigerant through the evaporator coil 60 and the condenser coil 61. The evaporator coil 60 is located inside the dehumidifier chamber 32. The condenser coil is located in the droplet chamber 34. The air conditioning compressor 62 is preferably located inside the bottom equipment space 30. Moisture in the air condenses on the evaporator coil 60 and then drops into a liquid collection bottle 64. Heat from the condenser coil 61 dries air going through the droplet chamber. A filtration unit 65 receives air from the droplet chamber 34. The air from the droplet chamber passes through the filtration unit 65. A diverter valve 66 is preferably located in the bottom equipment chamber 28. The diverter valve 66 includes a humidifier chamber inlet 68, a droplet chamber inlet 70 and an outlet 72. The diverter valve 66 shuttles between the humidifier chamber inlet 68 and the droplet chamber inlet 70. The outlet 72 of the diverter valve 66 is connected to an inlet of an air blower 74. An outlet 76 of the air blower 76 is connected to a heater 77. The heater 77 is connected to a diffuser 78. The diffuser 78 is preferably located in a bottom of the sealed test chamber 26. Air blowing upward from the diffuser 78 dries the products disinfected and tested in the sealed test chamber 26. The air from the diffuser 78 passes through a humidifier screen 80 and a droplet screen 82 near a top of the sealed test chamber 26. The air travels through the humidifier screen 80 into the dehumidifier chamber 32 and the droplet screen 82 into the droplet chamber 34. A vacuum pump 85 is preferably used to pull a vacuum on the sealed test chamber 26 before treatment of an electrical cable or component. The heater 77 may be used to remove any additional moisture not removed by the vacuum pump 85 in the sealed test chamber 26.

A disinfectant reservoir 84 and a water reservoir 86 are preferably located in the top equipment space 28. Disinfectant from the disinfectant reservoir 84 flows into a first inlet of a mixing device 88 and water from the water reservoir 86 flows into a second inlet of the mixing device 88. An outlet of the mixing device 88 is connected to the supply reservoir 50 of the aerosol generator 40. The disinfectant reservoir 84 and the water reservoir 86 may be filed through a fill port 90 outside the sealed test cabinet 10. Inlets (not shown) in a drain manifold 92 draw liquid from numerous places in the sealed test cabinet 10 and an outlet feeds the liquid into the liquid collection bottle 64. The liquid collection bottle 64 is preferably removed from a front of the sealed test cabinet 10. The aerosol control module 44 includes electronic devices needed to control the operation of the disinfection system 12, the dehumidifier 14 and communicates with an electronic test module 96 of the electrical function tester 16. The wireless control interface 18 preferably controls the operation of the aerosol control module 44 through a touch screen interface 94. The aerosol control module 44 preferably controls the electronic test module 96. The wireless control interface 18 includes wireless communication through Bluetooth and WIFI protocols.

The electrical function tester 16 preferably includes the electronic test module 96, a plurality of test sockets 98, a plurality of interface test blocks 102 and the bar code reader 20. The electronic test module 96 includes the compliance software 22, the tracking software 24 and software to inventory tested electrical cables or components and report compliance connected to one of the plurality of test sockets 98. An electrical cable 104 is retained in the interface test block 102. The interface test blocks 102 may be permanently electrically connected to electronic test module without the need for test sockets 98. The bar code reader 20 is used to read a bar code, radio frequency identification tag, or other electronically imbedded coding circuit, which is used to identify each electrical cable or component placed in the sealed test chamber 26. An output of the bar code reader 20 is connected to the electronic test module 96.

Figure 4:
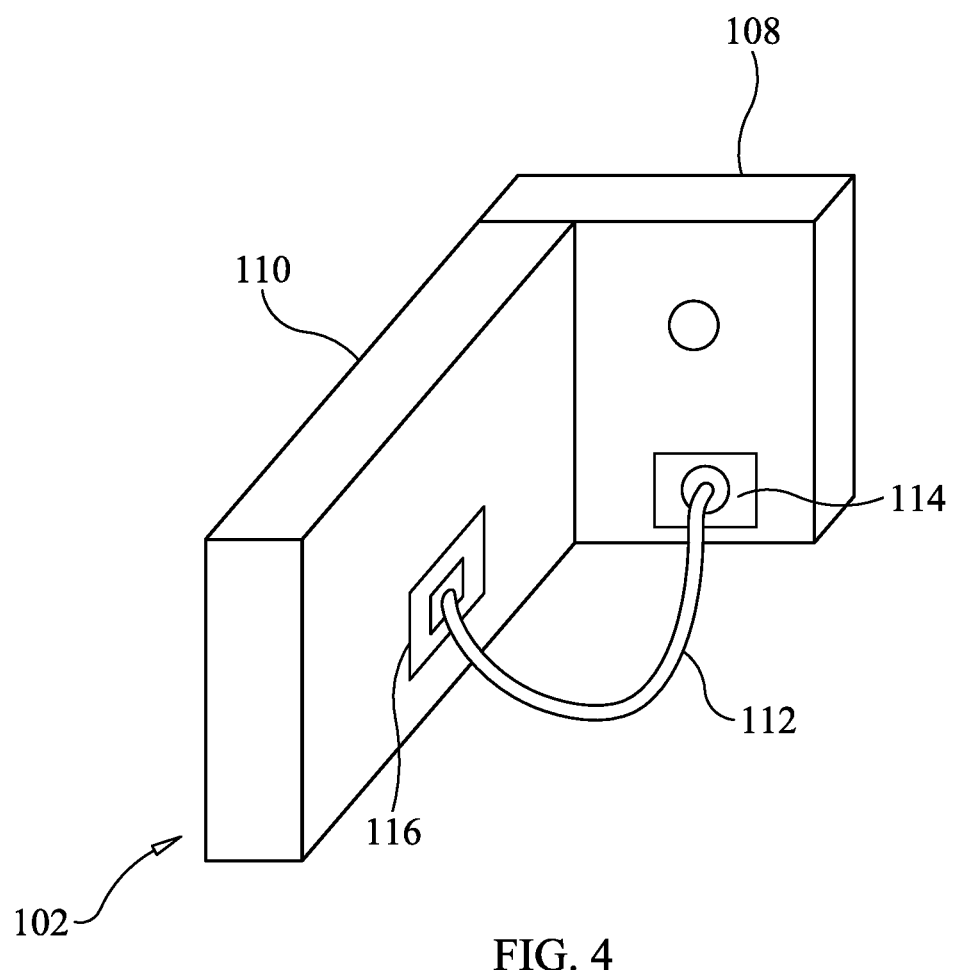
FIG. 4 is a perspective view of a interface test block with a cable inserted for testing in accordance with the present invention.

The plurality of interface test blocks 102 include an ECG interface test block, a SPO2 interface test block, a IBP interface test block, a TEMP interface test block and a TOCO interface test block. With reference to FIG. 4, each interface test block 102 preferably includes a base portion 108 and an extension portion 110, which extends from the base portion 108. When needed, the interface test block 102 will include a patient simulation device for providing feedback to a sensor of a particular cable. A plurality of connector pins (not shown) extend from a back of the base portion 108. The connector pins are plugged into one of the plurality of test sockets 98. One end of an electrical cable 112 is connected to a base socket 114 in the base portion 108 and an opposing end of the electrical cable 114 is connected to a extension socket 116 in the extension portion 110. The electronic test module 96 also tests the safety of the electrical cable 114. The electronic test module 96 is preferably located in the top equipment space 28. The inlets into the sealed test chamber 26 and the outlets from the sealed test chamber 26 are preferably sealed with check valves. HEPA filters are preferably used before the inlets and after the outlets to filter the air going into the sealed test chamber 26 and exhausting from the sealed test chamber 26.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A multi-function product cabinet for electrical testing and at least one of sanitizing, disinfecting, high level disinfecting and sterilization of at least one object, comprising:
   a test cabinet including a sealed test chamber and a sealed door that provides access to said sealed test chamber;
   a device for supplying a treatment substance for application to an outside surface of the at least one object tested in said sealed test chamber;
   an electrical function tester including an electronic test module and a plurality of interface test blocks, said plurality of interface test blocks are electrically connected to said electronic test module, said plurality of interface test blocks are located in said sealed test chamber, wherein the at least one object is electrically connected to at least one of said plurality of interface test blocks, said electronic test module tests electrical functionality of the at least one object; and
   an air blower for circulating air through said sealed test chamber.

2. The multi-function product cabinet of claim 1 wherein:
   a dehumidifier chamber is located behind said sealed test chamber, said dehumidifier chamber communicates with said sealed test chamber through a screen.

3. The multi-function product cabinet of claim 2 wherein:
   a droplet chamber is located behind said sealed test chamber, said droplet chamber communicates with said sealed test chamber through a screen, said droplet chamber is located adjacent said dehumidifier chamber.

4. The multi-function product cabinet of claim 3, further comprising:
   a diverter valve having a dehumidifier chamber inlet, a droplet chamber inlet and an outlet, said dehumidifier chamber communicates with said dehumidifier chamber inlet, said droplet chamber is coupled to said droplet chamber inlet through a filtration unit, said diverter valve chooses either said dehumidifier chamber input or said droplet chamber input for exhaust through said outlet.

5. The multi-function product cabinet of claim 3, further comprising:
   a diverter valve having a dehumidifier chamber inlet, a droplet chamber inlet and an outlet, said dehumidifier chamber communicates with said dehumidifier chamber inlet, said droplet chamber is coupled to said droplet chamber inlet through a filtration unit, said diverter valve chooses either said dehumidifier chamber input or said droplet chamber input for exhaust through said outlet.

6. The multi-function product cabinet of claim 5 wherein:
   an inlet of said air blower communicates with said outlet of said diverter valve, said air blower blows air into said sealed test chamber.

7. The multi-function product cabinet of claim 6, further comprising:
   a heater for heating the air from an outlet of said air blower.

8. The multi-function product cabinet of claim 1, further comprising:
   a bar code reader for reading identifying tag from the at least one object to be tested, said bar code reader is connected to said electronic test module.

9. The multi-function product cabinet of claim 1, further comprising:
   an aerosol control module for controlling the operation of said device for supplying a treatment substance and communicating with said electrical function tester.

10. The multi-function product cabinet of claim 9, further comprising:
    a wireless control interface for communicating with said aerosol control module.

11. A multi-function product cabinet for electrical testing and at least one of sanitizing, disinfecting, high level disinfecting and sterilization of at least one object, comprising:
    a test cabinet including a sealed test chamber and a sealed door that provides access to said sealed test chamber;
    an aerosol generator for supplying a treatment substance in the form of an aerosol to an outside surface of the at least one object tested in said sealed test chamber;
    an electrical function tester including an electronic test module and a plurality of interface test blocks, said plurality of interface test blocks are electrically connected to said electronic test module, said plurality of interface test blocks are located in said sealed test chamber, wherein the at least one object is electrically connected to at least one of said plurality of interface test blocks, said electronic test module tests electrical functionality of the at least one object;
    an air blower for circulating air through said sealed test chamber; and
    a vacuum pump for drawing a vacuum on said sealed test chamber.

12. The multi-function product cabinet of claim 11 wherein:
    a dehumidifier chamber is located behind said sealed test chamber, said dehumidifier chamber communicates with said sealed test chamber through a screen.

13. The multi-function product cabinet of claim 12 wherein:
  a droplet chamber is located behind said sealed test chamber, said droplet chamber communicates with said sealed test chamber through said screen, said droplet chamber is located adjacent said dehumidifier chamber.

14. The multi-function product cabinet of claim 12, further comprising:
  a dehumidifier including an evaporator coil, a condenser coil, an air conditioning compressor and refrigerant, said air conditioner pumps refrigerant through said evaporator and condenser coils, said evaporator coil is located in said dehumidifier chamber, said condenser coil is located in said droplet chamber, wherein heat from said condenser coil warms air passing through said droplet chamber.

15. The multi-function product cabinet of claim 13, further comprising:
  a diverter valve having a dehumidifier chamber inlet, a droplet chamber inlet and an outlet, said dehumidifier chamber communicates with said dehumidifier chamber inlet, said droplet chamber is coupled to said droplet chamber inlet through a filtration unit, said diverter valve chooses either said dehumidifier chamber input or said droplet chamber input for exhaust through said outlet.

16. The multi-function product cabinet of claim 15 wherein:
  an inlet of said air blower communicates with said outlet of said diverter valve, said air blower blows air into said sealed test chamber.

17. The multi-function product cabinet of claim 16, further comprising:
  a heater for heating the air from an outlet of said air blower.

18. The multi-function product cabinet of claim 11 wherein:
  said plurality of interface test blocks include at least one of an ECG interface test block, a SPO2 interface test block, a IBP interface test block, a TEMP interface test block and a TOCO interface test block.

19. The multi-function product cabinet of claim 11, further comprising:
  an aerosol control module for controlling the operation of said aerosol generator for supplying a treatment substance and communicating with said electrical function tester.

20. The multi-function product cabinet of claim 1 wherein:
  said treatment substance is one of UV light, vaporized hydrogen peroxide and Peroxyacetic Acid gas.

* * * * *